United States Patent
Müller

(10) Patent No.: US 9,504,792 B2
(45) Date of Patent: Nov. 29, 2016

(54) DISPENSING APPARATUS

(71) Applicant: Sulzer Mixpac AG, Haag (CH)

(72) Inventor: Marco Müller, Ebikon (CH)

(73) Assignee: SULZER MIXPAC AG, Haag (CH)

( * ) Notice: Subject to any disclaimer, the term of this patent is extended or adjusted under 35 U.S.C. 154(b) by 0 days.

(21) Appl. No.: 14/651,870

(22) PCT Filed: Nov. 27, 2013

(86) PCT No.: PCT/EP2013/074850
§ 371 (c)(1),
(2) Date: Jun. 12, 2015

(87) PCT Pub. No.: WO2014/090576
PCT Pub. Date: Jun. 19, 2014

(65) Prior Publication Data
US 2015/0314078 A1    Nov. 5, 2015

(30) Foreign Application Priority Data

Dec. 13, 2012  (EP) .................................... 12196842

(51) Int. Cl.
*A61M 5/32*         (2006.01)
*B65D 83/00*       (2006.01)
(Continued)

(52) U.S. Cl.
CPC ......... *A61M 5/3202* (2013.01); *A61M 5/3134* (2013.01); *B05C 17/00513* (2013.01); *B65D 47/265* (2013.01); *B65D 83/0033* (2013.01); *A61M 2005/3128* (2013.01); *A61M 2039/229* (2013.01)

(58) Field of Classification Search
CPC .......... A61M 5/3202; A61M 5/3134; A61M 2005/3128; A61M 2039/229; B05C 17/00513; B65D 47/265; B65D 83/0033
USPC ............ 222/545, 548; 604/183, 248, 89, 91, 604/191
See application file for complete search history.

(56) References Cited

U.S. PATENT DOCUMENTS 553,234 A    1/1896  Finot
1,831,668 A   11/1931 Juhl
(Continued)

FOREIGN PATENT DOCUMENTS

DE    102011111552 A1    9/2012
EP         0344956 A1   12/1989
(Continued)

*Primary Examiner* — Donnell Long
(74) *Attorney, Agent, or Firm* — Global IP Counselors, LLP

(57) ABSTRACT

A dispensing apparatus for a flowable component includes a storage container, an applicator and a closure element. The storage container has a storage chamber configured to receive the component, an outlet flange and a component outlet. The applicator has a component inlet and a dispensing opening, and is connected to the storage container by the outlet flange establishing a connection between the component outlet of the storage container and the component inlet of the applicator. The closure element is independent from the applicator, and configured to selectively adopt a closed position and a dispensing position, the component outlet is closed in the closed position and open in the dispensing position, and is configured to be coupled to the applicator so as to be brought from the closed position into the dispensing position by a rotation of the applicator in a connection direction with respect to the storage container.

20 Claims, 3 Drawing Sheets

(51) Int. Cl.
  *B65D 47/26* (2006.01)
  *B05C 17/005* (2006.01)
  *A61M 5/31* (2006.01)
  *A61M 39/22* (2006.01)

(56) References Cited

U.S. PATENT DOCUMENTS

| | | | |
|---|---|---|---|
| 5,078,691 A | 1/1992 | Hamacher | |
| 5,947,954 A * | 9/1999 | Bonaldo | A61M 39/22 |
| | | | 604/248 |
| 6,565,550 B1 * | 5/2003 | Klein | A61M 25/0097 |
| | | | 604/506 |
| 6,929,159 B1 * | 8/2005 | Haig | B65D 47/265 |
| | | | 141/18 |
| 2004/0256421 A1 * | 12/2004 | Werth | B65D 47/265 |
| | | | 222/480 |
| 2006/0014440 A1 | 1/2006 | Sogaro | |
| 2011/0139821 A1 * | 6/2011 | Greter | A61B 17/00491 |
| | | | 222/145.5 |
| 2011/0315720 A1 * | 12/2011 | Marshall | B29C 49/00 |
| | | | 222/568 |

FOREIGN PATENT DOCUMENTS

| | | |
|---|---|---|
| EP | 1616590 A1 | 1/2006 |
| EP | 1968751 B1 | 4/2011 |
| WO | 94/11039 A1 | 5/1994 |
| WO | 02/36033 A1 | 5/2002 |

* cited by examiner

DISPENSING APPARATUS

CROSS-REFERENCE TO RELATED APPLICATIONS

This application is a U.S. National stage application of International Application No. PCT/EP2013/074850, filed Nov. 27, 2013, which claims priority to EP Patent Application 12196842.4, filed Dec. 13, 2012, the contents of each of which are hereby incorporated herein by reference.

BACKGROUND

Field of the Invention

The invention relates to a dispensing apparatus for a flowable component.

Background Information

In DE 10 2011 111 552 A1 a dispensing apparatus for a flowable component in the form of a syringe is described. The dispensing apparatus has a storage container in the form of a syringe cylinder having a storage chamber for the reception of the component, an outlet flange and a component outlet. An applicator in the form of a needle can be placed onto the storage container, which applicator has a component inlet and a dispensing opening. The outlet flange has an inner thread and the applicator has a corresponding outer thread, so that the applicator can be screwed onto the storage container. For closing the component outlet of the storage container a separate closure cap is provided which has to be removed prior to the screwing onto the applicator. If the component outlet has to be closed again the closure cap has to be stored safely so that it can be placed thereon again.

SUMMARY

In contrast to this it is, in particular the object of the invention to provide a dispensing apparatus which can be handled in a simple manner. In accordance with the invention this object is satisfied by a dispensing apparatus having the features of the described here-in.

The dispensing apparatus for a flowable component has a storage container having a storage chamber for the reception of the component, an outlet flange and a component outlet. It moreover has an applicator having a component inlet and a dispensing opening.

The applicator can be connected to the storage container via the outlet flange, whereby a connection between the component outlet of the storage container and the component inlet of the applicator can be established. The applicator can thus be placed onto the storage container.

In accordance with the invention the dispensing apparatus has a closure element independent from the applicator which closure element can adopt a closed position and a dispensing position. "Independent" in this connection should be understood such that the applicator and the closure element are of two-piece design and can be moved independent of one another. In the closed position of the closure element, the component outlet of the storage container is closed and in the dispensing position it is opened. The closure element can be coupled to the applicator such that it can be placed from the closed position into the dispensing position by a rotation of an applicator in the connection direction with respect to the storage container. In this connection the coupling takes place during the placing of the applicator onto the storage container.

In this way only one step is required for preparing a dispensing of the component from the storage chamber. During the placing of the applicator onto the storage container the closure element is simultaneously brought into the dispensing position and in this way the component outlet is opened. The closure cap of the dispensing apparatus in accordance with the DE 10 2011 111 552 A1 has to be initially removed and only thereafter can the applicator be placed thereon. Despite the simple handling capability of the dispensing apparatus no further components are required. Instead of a closure cap the closure element is used for the closing of the component outlet.

The applicator is, in particular configured as a needle or as a cannula. However, it can also have any other arbitrary shape, thus, for example, be configured as a tube having a brush at the tip.

The dispensing apparatus is, in particular, made of plastic, for example polyethylene, polypropylene or polyamide, by means of an injection molded process. It is, in particular provided to receive between 0.5 and 5 ml of the component. It can, in particular be used in the medical field, in particular in the dental field. However, also other fields of application, for example for adhesives are plausible.

The dispensing apparatus is, in particular provided for the dispensing of only one component. However, it is also plausible that the storage container has two separate storage chambers for two different components, which should be mixed during the dispensing. In this case, the applicator is, in particular configured as a mixing apparatus having a mixer element.

In an embodiment of the invention the applicator can be removed after a rotation against the connection direction from the storage container. In this connection, one assumes a plugged position of the applicator, this means a position in which the applicator is connected to the storage container such that the component can be dispensed. Through the said rotation against the connection direction the closure element can again be brought from the dispensing position into the closed position. In this way, an opened component outlet can be closed again in a simple kind and manner. In this way it is possible in a simple manner to not only dispense the component in one go, but also in partial amounts and there between to reclose the component outlet again. On dispensing always the same applicator or, in particular new applicators, can be used.

For a dispensing apparatus in accordance with DE 10 2011 111 552 A1 after removal of the applicator, the closure cap has to be always screwed on again which would represent an additional work step. Moreover, the closure cap has to be so safely secured that it can be placed thereupon again.

It is possible that a seal of the component outlet, for example, in the form of a closure cap or of a foil is provided for a long time storage. If the component should not be dispensed at once, the dispensing apparatus in accordance with the invention enables a simple handling, since for a short term storage a simple closure of the component outlet is possible after a first time opening by means of the closure element.

In an embodiment of the invention the connection between the applicator and the storage container can be established by said rotation of the applicator in the connection direction with respect to the storage container for the setting of the dispensing position of the closure element. In this way, the connection of the applicator to the storage container, this means the plugging onto of the storage container and the opening of the component outlet takes place simultaneously, such that for both only one work step and/or hand grip is required. This enables a particularly simple handling of the dispensing apparatus.

The applicator, in particular has an outer thread and the outlet flange of the storage container has a corresponding inner thread. In this way a secure connection between the applicator and the storage container can be manufactured in a simple manner. When the thread is carried out as a multi-start thread the thread can have a large pitch. In this way, a large stroke can be generated for a small rotation and the applicator can thus be completely placed with only a small rotation, for example, by a quarter of a rotation. The thread can, in particular be configured as a two start thread. A multi-start thread in this connection is to be understood such that a plurality of threads are arranged in parallel to one another.

It is also possible that the connection between the outlet flange of the storage container and the applicator is produced by means of a bayonet closure or a sleeve nut.

In an embodiment of the invention the closure element has an entrainer pin and the applicator has a corresponding entrainer recess. These are configured and arranged such that on a placing of the applicator onto the storage container, the entrainer pin dips into the entrainer recess such that the closure element is entrained on a rotation of the applicator with respect to the storage container. In this way, a simple and cost-effective realization of the coupling between the applicator and the closure element is possible. Moreover, the applicator can thus also be used at different dispensing apparatuses without a closure element in accordance with the embodiments disclosed herein. The used applicator is thus universally applicable and can therefore be manufactured in large numbers and therefore cost-effectively.

"Entrainment" in this connection should, in particular be understood such that the entrainment pin likewise carries out a rotary movement. However, it is also possible that the recess is configured such that the entrainer pin can be displaced along an axis.

In an embodiment of the invention the storage container has a middle axis which extends through the component outlet. The storage container, in particular has a hollow cylindrical basic shape such that the storage container is generally configured cylindrical and in this way has a circular cross-section. In this case, a middle axis is to be understood as an axis which passes through the center points of the individual cross-sections. For a quadratic, rectangular or elliptical shaped cross-section of the storage chamber, an axis is understood such that it passes through the crossing points of the two axes of symmetries of the individual cross-sections. The closure element is rotated about an axis of rotation on a change from the closed position into the dispensing position which axis of rotation is arranged spaced apart from the middle axis of the storage container. The closure element is thus eccentrically arranged with respect to the storage chamber. In this way, a simple assembly of the dispensing apparatus is possible.

In an embodiment of the invention the closure element has a recess which is positioned in the dispensing position of the closure element such that the component can flow from the storage chamber to the component inlet of the applicator via the component outlet and the recess. In the closed position the recess is no longer positioned in such a manner that the component outlet is closed. In this way, a simple construction of the closure element is enabled.

In an embodiment of the invention the storage chamber has a guide pin. The recess of the closure element is configured and arranged such that the guide pin is arranged in the recess both in the closed position and in the dispensing position. In this way, on the one hand, a guidance of the closure element during the change from the closed position and back is ensured and, on the other hand, the recess can be configured such that the guide pin abuts at the recess of the closure element in the closed position and in the dispensing position of the closure element, whereby the two positions can be precisely defined. Additionally, a storage cam can be provided at the storage chamber or at the applicator and two recesses can be provided at the respective other part in which recesses the storage cam can latch in the closed position and/or the dispensing position and thus additional define the two positions.

In an embodiment of the invention the closure element is configured as a closure disc which is at least partly arranged in the closure recess of the storage container. The closure element, in particular has a circular outer contour. It can thus also be completely arranged within the closure recess. In this way, a simple construction of the dispensing apparatus is enabled.

The closure recess, in particular has a retaining element which cooperates with the closure element such that the closure element is captively held in the closure recess after insertion. In this way, it can be ensured that the closure element cannot be released from the closure recess accidently and thus open the component outlet unintentionally. The retaining element is, in particular configured as one or more bulges facing in the direction of the axis of rotation of the closure element. The bulges can be configured as so-called noses or as a sectionally or completely surrounding collars. This enables a simple and cost-effective design of the retaining element.

In an embodiment of the invention the closure element has an edge at its outer contour and thus not at its end face which edge cooperates with the retaining element of the storage container. The said edge, in particular arises thereby that the diameter of the closure element increases jump-like in the direction of the storage chamber.

The closure element, in particular has an introduction inclination which is oriented in the direction of the storage chamber. In this way, a simple insertion of the closure element into the closure recess is possible.

Further advantages, features and particulars of the invention result with reference to the following description of embodiments, as well as with reference to the drawing, in which the same or functionally equal elements are provided with identical reference numerals.

BRIEF DESCRIPTION OF THE DRAWINGS

The invention will be explained in more detail in the following with reference to the drawing. There is shown.

DETAILED DESCRIPTION OF EMBODIMENTS

Figure 1:
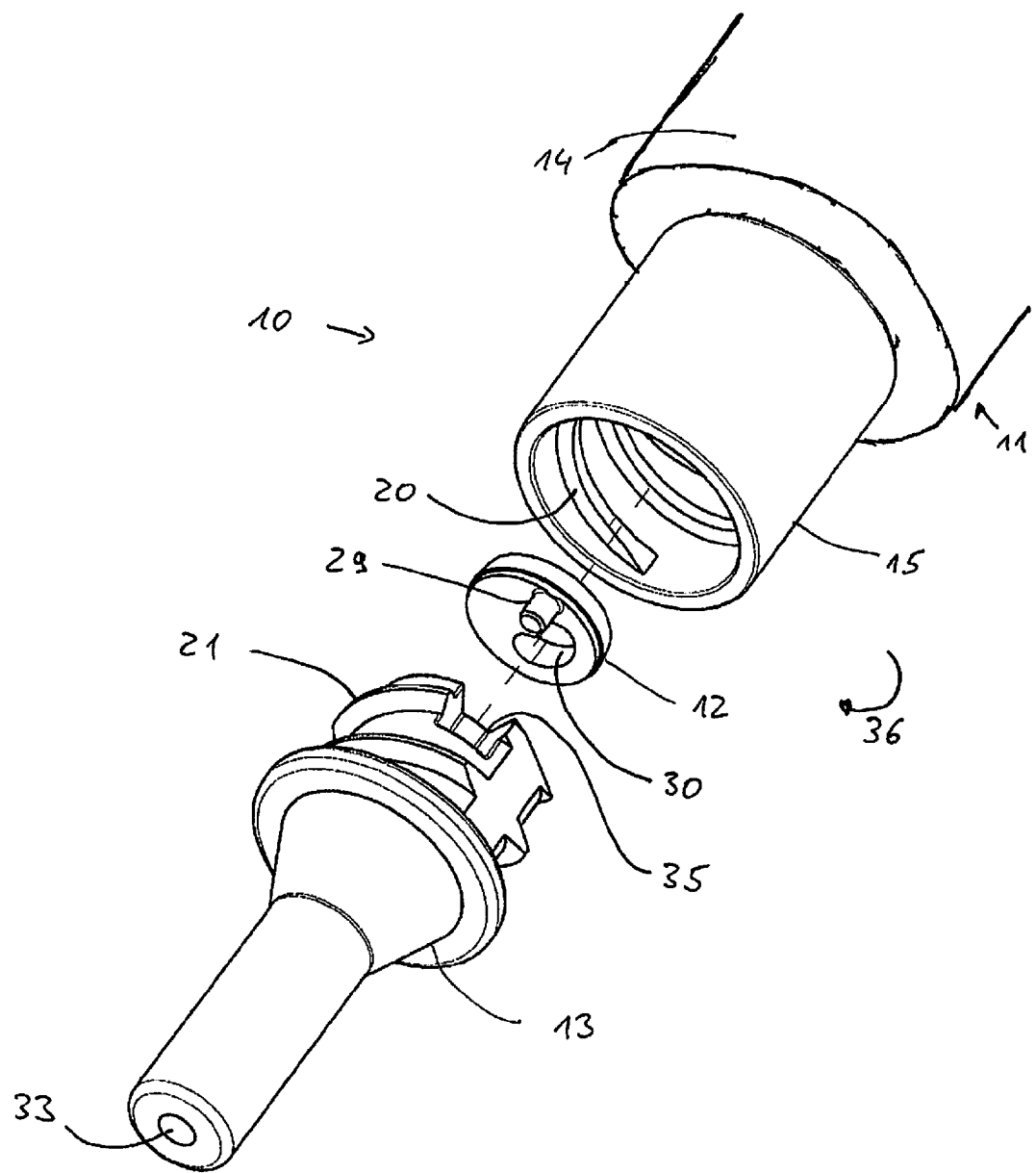
FIG. 1 is an exploded illustration of a section of a dispensing apparatus.
Figure 2:
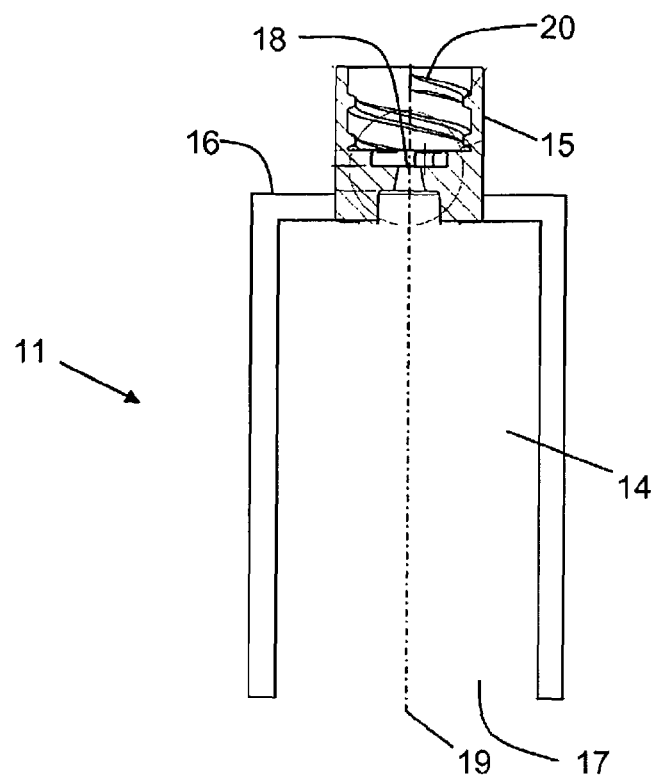
FIG. 2 is a storage container of the dispensing apparatus of FIG. 1 in a sectional illustration.
Figure 3:
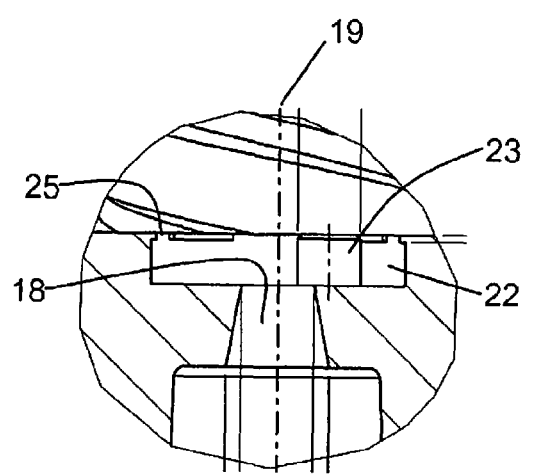
FIG. 3 is a detail of the storage container of FIG. 2.

In accordance with FIG. 1 a dispensing apparatus 10 includes a storage container 11, a closure element 12 and an applicator 13. The storage container 11 illustrated in FIG. 2 in a section has a cylindrical storage chamber 14 and an outlet flange 15 which is arranged at a planar top side 16 of the container 11. Opposite the top side 16, the storage container 11 has an inlet opening 17 via which a flowable component can be filled into the storage chamber 14. A non-illustrated piston is inserted via the filling opening 17 after the filling of the component, which piston, on the one hand, terminates the storage chamber 14 and, on the other hand, can be displaced for the dispensing of the component in the direction of the top side 16 of the storage container.

A component outlet 18 is arranged within the outlet flange 15 via which the components can exit from the storage chamber 14. The component outlet 18 is of circular design and is arranged centrally with respect to the storage chamber 14, such that a middle axis 19 of the storage container 11 runs centrally through the component outlet 18. The middle axis 19 corresponds to the axis of symmetry of the storage chamber 14 which extends through the middle point of the circular cross-section of the storage chamber.

The applicator 13 can be connected to the storage container 11 by the outlet flange 15. The outlet flange 15 has an inner thread 20 for this purpose and the applicator has an outer thread 21 which is configured as a two start thread. The inner thread 20 and the outer thread 21 are configured such that the applicator 13 can be completely screwed onto the storage chamber within a little more than a quarter of a rotation.

Figure 4:
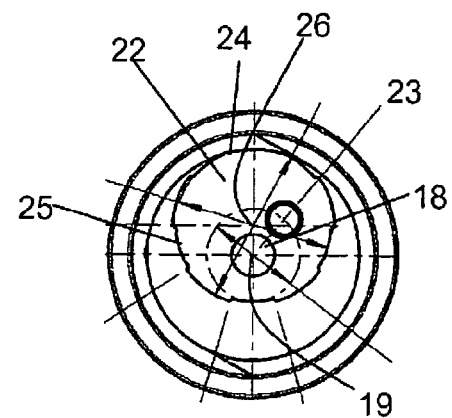
FIG. 4 is the storage container of FIG. 2 in a top view.

The component outlet 18 can be closed by means of the closure element 12 which is configured as a closure disc. The closure element 12 is arranged in a closure recess 22 of the outlet flange 15 open in a direction of the applicator 13 for this purpose and is thus arranged in the storage container 11. The closure recess 22 has a generally circularly cross-section as illustrated in FIG. 4, and is arranged displaced with respect to this middle axis 19 of the storage container 11. A cylindrical guide pin 23 is arranged within the closure recess 22. The guide pin 23 is configured of one piece design with the storage container 11, arranged in parallel to the middle axis 19 and projects in the direction of the applicator 13. At the collar 24 resulting in the direction of the applicator 13 the closure recess 22 has a plurality retaining elements 25 which are respectively configured as a partially surrounding collar. The retaining elements 25 for this purpose serve, to captively hold a closure element 12 inserted in the retaining recess 22.

Figure 5:
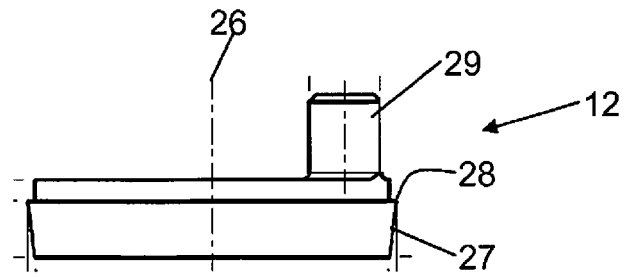
FIG. 5 is a closure element of a dispensing apparatus of FIG. 1 in a sectional illustration.
Figure 6:
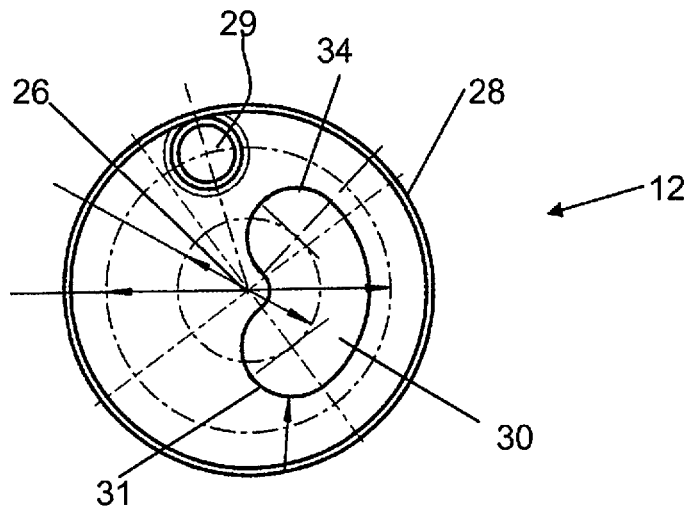
FIG. 6 is the closure element of FIG. 5 in a top view.

In accordance with FIG. 5 and FIG. 6 the closure element 12 has a generally cylindrical basic shape corresponding to the closure recess 22. With respect to a longitudinal axis which also simultaneously illustrates an axis of rotation 26 of the closure element 12, a total of three regions are to be differentiated. In the first region, in the direction of the storage chamber 14 the diameter of the closure element 12 becomes slightly larger in the direction of the applicator 13 such that an introduction inclination 27 arises. At the transition to the second region the diameter of the closure element 12 reduces in a jumped manner such that an edge 28 is formed at its outer contour. The diameter of the closure element 12 is constant in the second region. The third region of the closure element 12 is formed by an entrainer pin 29 which has a cylindrical basic shape and which, in the assembled state, is oriented parallel to the axis of rotation 26. The entrainer pin 29 is directly arranged at the boundary of the closure element 12. The closure recess 22 and the closure element 12 are configured such that in the mounted state of the closure element 12 the edge 28 latches beneath the retaining element 25 such that the closure element 12 cannot fall out of the closure recess 22.

As illustrated in FIG. 6 the closure element 12 has a continuous recess 30 in the direction of the axis of rotation which recess has a shape which is similar to the shape of a kidney. In the mounted state of the closure element 12, the guide pin 23 projects into the recess 30 such that it can be arranged within the recess 30. The closure element 12 can adopt a closed position and a dispensing position, wherein a change between the said positions can be made by a rotation of the closure element 12 about the axis of rotation 26. In this connection, the axis of rotation 26 is in parallel to, but spaced apart from the middle axis 19 of the storage container 11 and in this way is eccentrically arranged with respect to the storage container 11.

In the closed position of the closure element 12 the component outlet 18 is closed by the closure element 12 thus, no covering between the component outlet 18 and the recess 30 of the closure element 12 exists. In this connection, the guide pin 23 of the storage chamber 11 abuts at a first end 31 of the recess 30 of the closure element 12 which closure element is arranged spaced apart further from the entrainer pin 29 with respect to a second end 34. In order to change from the closed position into the dispensing position the closure element 12 is rotated by approximately 100° in the clock-wise direction about the axis of rotation 26 until the guide pin 23 of the storage chamber 11 abuts at the second end 34 of the recess 30 of the closure element 12. The cooperation between the recess 30 of the closure element 12 and the guide pin 23 in this way defines the closed position and the dispensing position and the guide pin 23 is arranged both in the closed position and in the dispensing position in the recess 30.

Figure 7:
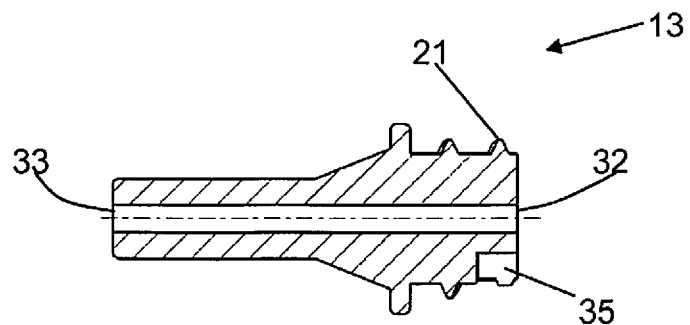
FIG. 7 is an applicator of the dispensing apparatus of FIG. 1 in a sectional illustration.

In the dispensing position the recess 30 of the closure element 12 is arranged in front of the component opening 18. In this dispensing position of the closure element 12 the component can be dispensed from the storage chamber 14 via the component outlet 18 of the storage container 11, the recess 30 of the closure element 12, a component inlet 32 and a dispensing opening 33 of the applicator 13 (see FIG. 7). In order to arrive again in the closed position from the dispensing position, the closure element 12 can be rotated back by the said approximately 100° against the clockwise direction.

The torque required for the rotation of the closure element 12 is transmitted via the applicator 13 and the entrainer pin 29 onto the closure element 12. The applicator 13 has an entrainer recess 35 for this purpose at its end oriented in the direction of the storage container 11. The entrainer recess 35 is configured as a cutout in the outer thread 21 of the applicator 13 open in the direction of the storage container 11 and extending in the direction of the middle axis 19 of the storage chamber 11. It is dimensioned such that the entrainer pin 29 of the closure element 12 can dip into the outlet flange 15 on a plugging onto of the applicator and can be entrained on a rotation of the applicator 13 with respect to the storage container 11.

The closure element 12 is placed into the closed position on the mounting of the dispensing apparatus 11, such that in a subsequent step the component is filled in the thus closed storage chamber 14 at the dispensing flange 15 and the non-illustrated piston can be inserted. The entrainer pin 29 of the closure element 12 is in this way positioned such that it dips into the entrainer recess 35 of the applicator 13 on a positioning of the applicator 13. On rotating the applicator 13 in the clock-wise direction and in this way in a connection direction 36 in the outlet flange 15 the entrainer pin 29 is entrained by the applicator 13 and in this way the closure element 12 is rotated about the axis of rotation 26 in the clock-wise direction and in this way the dispensing position is set, such that the component can be dispensed from the storage chamber 14 via the dispensing opening 33 of the applicator 13. The turning of the applicator 13 typically takes place by hand. If the component should not be completely dispensed but a part should only be dispensed at a latter point in time, then the component opening and in this way the storage chamber 14 can be closed again by a removal of the applicator 13. Through a rotation of the applicator 13 against the connection direction 36 the entrainer pin 29 is again entrained and in this way the closure element 12 is rotated about the axis of rotation 26 against the clock-wise direction and in this way the closed position is set again. Only when the closed position is achieved, can the applicator be removed from the dispensing flange 15. In this way, it is ensured that the component outlet 18 is always closed when the applicator 13 is removed.

The invention claimed is:

1. A dispensing apparatus for a flowable component, the dispensing apparatus comprising:
    a storage container having a storage chamber configured to receive the component, an outlet flange, a component outlet and a middle axis extending through the component outlet;
    an applicator having a component inlet and a dispensing opening,
        the applicator being connected to the storage container by the outlet flange establishing a connection between the component outlet of the storage container and the component inlet of the applicator; and
    a closure element independent from the applicator, the closure element configured to selectively adopt a closed position and a dispensing position, the component outlet of the storage container being closed in the closed position and being open in the dispensing position,
        the closure element being configured to be coupled to the applicator so as to be brought from the closed position into the dispensing position by a rotation of the applicator in a connection direction with respect to the storage container, and
        the closure element being configured to be rotated about an axis of rotation on changing from the closed position into the dispensing position, the axis of rotation being arranged spaced apart from the middle axis of the storage container.

2. The dispensing apparatus in accordance with claim 1, wherein the applicator is configured to be removed from the storage container after a rotation against the connection direction and the closure element is configured to be brought from the dispensing position into the closed position by the rotation against the connection direction.

3. The dispensing apparatus in accordance with claim 1, wherein the connection between the applicator and the storage container is established by the rotation of the applicator in the connection direction with respect to the storage container for setting the dispensing position of the closure element.

4. The dispensing apparatus in accordance with claim 3, wherein the applicator has an outer thread and the outlet flange of the storage container has a corresponding inner thread.

5. The dispensing apparatus in accordance with claim 4, wherein the outer thread and the inner thread are multi-start threads.

6. The dispensing apparatus in accordance with claim 1, wherein the closure element has an entrainer pin and the applicator has a corresponding entrainer recess which are configured and arranged such that, on a placement of the applicator onto the storage container, the entrainer pin dips into the entrainer recess such that the closure element is entrained on a rotation of the applicator with respect to the storage container.

7. The dispensing apparatus in accordance with claim 1, wherein the closure element has a recess which, in the dispensing position of the closure element, is positioned such that the component can flow out of the storage chamber via the component outlet and the recess to the component inlet of the applicator.

8. The dispensing apparatus in accordance with claim 7, wherein the storage chamber has a guide pin and the recess of the closure element is configured and arranged such that the guide pin is arranged in the recess both in the closed position and in the dispensing position.

9. The dispensing apparatus in accordance with claim 1, wherein the closure element is configured as a closure disc, is the closure disc being at least partly arranged in a closure recess of the storage container.

10. The dispensing apparatus in accordance with claim 9, wherein the closure recess has a retaining element cooperating with the closure element such that the closure element is maintained in the closure recess in a captive manner after insertion into the closure recess.

11. The dispensing apparatus in accordance with claim 9, wherein the closure element has an edge at an outer contour, the edge cooperating with the retaining element of the storage container.

12. The dispensing apparatus in accordance with claim 9, wherein the closure element has an introduction inclination.

13. A dispensing apparatus for a flowable component, the dispensing apparatus comprising:
    a storage container having a storage chamber configured to receive the component, an outlet flange and a component outlet;
    an applicator having a component inlet and a dispensing opening,
        the applicator being connected to the storage container by the outlet flange establishing a connection between the component outlet of the storage container and the component inlet of the applicator; and
    a closure element independent from the applicator, the closure element configured to selectively adopt a closed position and a dispensing position, the component outlet of the storage container being closed in the closed position and being open in the dispensing position,
        the closure element being configured to be coupled to the applicator so as to be brought from the closed position into the dispensing position by a rotation of the applicator in a connection direction with respect to the storage container, and
        the closure element having an entrainer pin and the applicator having a corresponding entrainer recess which are configured and arranged such that, on a placement of the applicator onto the storage container, the entrainer pin dips into the entrainer recess such that the closure element is entrained on a rotation of the applicator with respect to the storage container.

14. The dispensing apparatus in accordance with claim 13,
    wherein the applicator is configured to be removed from the storage container after a rotation against the connection direction and the closure element is configured to be brought from the dispensing position into the closed position by the rotation against the connection direction.

15. The dispensing apparatus in accordance with claim 13,
wherein the connection between the applicator and the storage container is established by the rotation of the applicator in the connection direction with respect to the storage container for setting the dispensing position of the closure element.

16. The dispensing apparatus in accordance with claim 13,
wherein the closure element is configured as a closure disc, is the closure disc being at least partly arranged in a closure recess of the storage container.

17. A dispensing apparatus for a flowable component, the dispensing apparatus comprising:
a storage container having a storage chamber configured to receive the component, an outlet flange and a component outlet;
an applicator having a component inlet and a dispensing opening,
the applicator being connected to the storage container by the outlet flange establishing a connection between the component outlet of the storage container and the component inlet of the applicator; and
a closure element independent from the applicator, the closure element configured to selectively adopt a closed position and a dispensing position, the component outlet of the storage container being closed in the closed position and being open in the dispensing position,
the closure element being configured to be coupled to the applicator so as to be brought from the closed position into the dispensing position by a rotation of the applicator in a connection direction with respect to the storage container,
the closure element having a recess which, in the dispensing position of the closure element, is positioned such that the component is capable of flowing out of the storage chamber via the component outlet and the recess to the component inlet of the applicator, and
the storage chamber having a guide pin and the recess of the closure element is configured and arranged such that the guide pin is arranged in the recess both in the closed position and in the dispensing position.

18. The dispensing apparatus in accordance with claim 17,
wherein the applicator is configured to be removed from the storage container after a rotation against the connection direction and the closure element is configured to be brought from the dispensing position into the closed position by the rotation against the connection direction.

19. The dispensing apparatus in accordance with claim 17,
wherein the connection between the applicator and the storage container is established by the rotation of the applicator in the connection direction with respect to the storage container for setting the dispensing position of the closure element.

20. The dispensing apparatus in accordance with claim 17,
wherein the closure element is configured as a closure disc, the closure disc being at least partly arranged in a closure recess of the storage container.

* * * * *